(12) United States Patent  
Coyle et al.

(10) Patent No.: US 8,729,510 B2  
(45) Date of Patent: *May 20, 2014

(54) ION BEAM SAMPLE PREPARATION APPARATUS AND METHODS

(71) Applicant: Gatan, Inc., Pleasanton, CA (US)

(72) Inventors: Steven Thomas Coyle, Alameda, CA (US); John Andrew Hunt, Fremont, CA (US)

(73) Assignee: Gatan Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/867,092

(22) Filed: Apr. 21, 2013

(65) Prior Publication Data

US 2013/0228708 A1 Sep. 5, 2013

Related U.S. Application Data

(63) Continuation of application No. 13/082,370, filed on Apr. 7, 2011, now Pat. No. 8,445,874.

(60) Provisional application No. 61/322,870, filed on Apr. 11, 2010.

(51) Int. Cl.
*H01J 37/20* (2006.01)

(52) U.S. Cl.
USPC ............ 250/492.3; 250/492.21; 250/309

(58) Field of Classification Search
CPC ................... G21K 7/00; H01J 37/20
USPC ...................................... 250/492.3
See application file for complete search history.

(56) References Cited

U.S. PATENT DOCUMENTS

| | | | |
|---|---|---|---|
| 4,272,682 A * | 6/1981 | Swann | 250/442.11 |
| 5,472,566 A | 12/1995 | Swann et al. | |
| 5,907,157 A | 5/1999 | Yoshioka et al. | |
| 5,922,179 A | 7/1999 | Mitro et al. | |
| 5,986,264 A | 11/1999 | Grunewald | |
| 6,406,589 B1 | 6/2002 | Yanagisawa | |
| 6,768,110 B2 | 7/2004 | Alani | |
| 6,784,427 B1 | 8/2004 | Grunewald et al. | |
| 6,914,244 B2 | 7/2005 | Alani | |
| 7,354,500 B2 | 4/2008 | Yoshioka et al. | |
| 7,573,047 B2 * | 8/2009 | Suzuki | 250/442.11 |
| 8,445,874 B2 * | 5/2013 | Coyle et al. | 250/492.3 |
| 2005/0081997 A1 | 4/2005 | Yoshioka et al. | |
| 2005/0118065 A1 | 6/2005 | Hasegawa et al. | |
| 2006/0255295 A1 | 11/2006 | Yoshioka et al. | |

* cited by examiner

*Primary Examiner* — Phillip A Johnston
(74) *Attorney, Agent, or Firm* — Theodore Heske, III

(57) ABSTRACT

Disclosed are embodiments of an ion beam sample preparation apparatus and methods for using the embodiments. The apparatus comprises an ion beam irradiating means in a vacuum chamber that may direct ions toward a sample, a shield blocking a portion of the ions directed toward the sample, and a shield retention stage with shield retention means that replaceably and removably holds the shield in a position. The shield has datum features which abut complementary datum features on the shield retention stage when the shield is held in the shield retention stage. A retention stage lifting means allows the creation of a loading chamber that is isolated from the main vacuum chamber where sample ion beam milling takes place. A heat sink means is configured to conduct heat away from the sample undergoing sample preparation in the ion beam.

25 Claims, 9 Drawing Sheets

ION BEAM SAMPLE PREPARATION APPARATUS AND METHODS

CROSS REFERENCE TO RELATED APPLICATIONS

This application is a continuation of prior filed non-provisional utility application Ser. No. 13/082,370 filed Apr. 7, 2011. Non-provisional utility application Ser. No. 13/082,370 claims the benefit of prior filed provisional Application No. 61/322,870 filed Apr. 11, 2010. Application Ser. No. 13/082,370 is incorporated herein by reference. Application No. 61/322,870 is incorporated herein by reference.

STATEMENT REGARDING FEDERALLY SPONSORED RESEARCH OR DEVELOPMENT

Not Applicable.

DESCRIPTION OF ATTACHED APPENDIX

Not Applicable.

BACKGROUND

The present disclosure relates to the use of one or more ion beams to prepare materials for microscopic observation or spectroscopic analysis. Microscopic observational techniques include, but are not limited to, optical microscopy, scanning electron microscopy (SEM), transmission electron microscopy (TEM), scanning transmission electron microscopy (STEM), reflection electron microscopy (REM). Spectroscopic analysis techniques include, but are not limited to, x-ray micro-analysis, reflection electron energy-loss spectroscopy (REELS), electron back-scattered diffraction (EBSD), x-ray photoelectron spectroscopy (XPS), and Auger electron spectroscopy (AES). Materials to be viewed under any microscopic technique may require processing to produce a sample suitable for microscopic examination.

Ion beam milling of a material can produce samples that are well suited for microscopic examination. An ion beam irradiating device may generate, accelerate, and direct a beam of ions toward a sample. The impact of ions on the sample sputters material away from the area of ion impact. Furthermore, the sample surface may be polished by the ion beam to a substantially smooth condition further enhancing observational properties of the sample. Regions of interest in the sample may be exposed and polished by the use of ion beams thus making a suitable observational sample from the material under investigation.

Broad Ion Beam Slope-Cutting (BIBSC), also known as cross section cutting using broad ion beam sources or cross section polishing using broad ion beam sources, is a rapid method for removing sample material to expose a smooth and substantially artifact-free cross-sectional surface for ultimate analysis by various microscopies and spectroscopies. A notable advantage of the BIBSC technique is high rates of surface preparation that can exceed tens or hundreds or thousands of square microns per hour, often over sample milling times of tens or hundreds of minutes.

Important considerations to users of the BIBSC technique include: reducing or minimizing the effort and time that the user is occupied in processing the sample; reducing or minimizing the number of steps where delicate samples are directly handled and at risk for damage, such as during mounting to sample holders for processing or analysis; reducing or minimizing the time and effort the user is occupied transferring the sample into the ultimate analysis equipment (imaging or spectroscopy), and aligning the coordinates of the prepared sample region to the ultimate analysis equipment prior to analysis; ensuring high quality and high probability of success in processing and imaging the sample; reducing or minimizing the time that the BIBSC ion milling equipment and sample mounting equipment are occupied for each sample; and ensuring high-quality microscopy observation of the sample during sample mounting and ultimate analysis by reducing the working distance required between the sample and the objective or probe-forming lens used for observation.

Ion beam milling takes place in a suitably evacuated environment. While a sample may be loaded and unloaded by the user at atmospheric pressure, ion beam processing must take place under vacuum like conditions. A near-vacuum environment that is suitable for ion beam milling of samples takes time to establish. The time required to obtain a suitably evacuated environment is proportional to the volume that must be evacuated prior to the commencement of ion beam milling. Embodiments of the present disclosure teach apparatus and methods of sample loading and processing that reduce the evacuated volume during sample loading and unloading, thereby enabling greater efficiencies in the processing of samples.

While a sample is being prepared in the ion beam, it may experience heating. Heating may alter the sample in ways that are undesirable. It may be the case, for example, that heating the sample softens or melts the sample, thereby causing alterations in the sample that would not happen if the temperature were maintained in a desirable range. Embodiments of the present disclosure teach apparatus, and methods of using that apparatus, to manage the thermal environment of a sample. Embodiments of improved thermal control over the sample may be beneficially combined with embodiments offering improved sample loading and processing to achieve even greater efficiencies in the processing of samples.

In consideration of the foregoing points, it is clear that embodiments of the present disclosure confer numerous advantages and are therefore highly desirable.

SUMMARY

The present disclosure is directed to ion beam sample preparation apparatus and methods for using the disclosed apparatus to prepare samples for later observation. The apparatus has features to quickly and repeatably retain and release both unprepared samples and prepared samples, thereby facilitating preparation of samples in the ion beam apparatus and also facilitating the observation of the prepared samples in an observation apparatus. Features of the disclosure enable accurate and repeatable positioning of the sample both within the ion beam sample preparation apparatus and within observation apparatus later used for observing prepared samples. Sample loading and processing features of the present disclosure work to reduce the volume requiring evacuation after sample loading. Sample loading and processing features also work to maintain a vacuum-like environment in a substantial portion of the vacuum chamber, even while the sample is being loaded at atmospheric pressure. Thermal management features of the present disclosure work to manage the thermal environment of the sample being prepared. The temperature of the sample undergoing ion beam sample preparation may thereby be influenced by the thermal environment created by the apparatus.

An embodiment according to the present disclosure of an apparatus for ion beam sample preparation comprises: an ion beam irradiating means disposed in a vacuum chamber and directing an ion beam toward a shield retention stage; the shield retention stage being disposed in the vacuum chamber; said shield retention stage comprising: a first datum feature; a second datum feature; a shield retention means having at least a shield releasing position and a shield retaining position; a retention stage lifting means coupled to said shield retention stage and configured to move said shield retention stage between a retention stage loading position and a retention stage processing position, characterized in that when the retention stage lifting means is in said retention stage loading position, a substantially vacuum-tight loading chamber is created between the shield retention stage and a portion of the vacuum chamber, and further characterized in that when the retention stage lifting means is in said retention stage loading position, a substantially vacuum-tight seal is created between the loading chamber and the portion of the vacuum chamber in which the ion beam irradiating means is disposed; a lift drive coupled to said retention stage lifting means and operable to move said retention stage lifting means between said retention stage loading position and said retention stage processing position; a removable and replaceable chamber cover disposed to allow access to said loading chamber when said retention stage lifting means is held in said retention stage loading position, characterized in that said chamber cover provides a substantially vacuum-tight seal when in place on said vacuum chamber; a shield having at least a rigid planar portion, removably and replaceably held in said shield retention stage, said shield further comprising: a proximal sample surface configured to durably adhere the sample to the shield; a first shielding surface disposed in the path of the ion beam and positioned to shield a portion of the ion beam directed at the sample when said shield is held in the shield retaining position of the shield retention means and the retention stage lifting means is held in the retention stage processing position; a third datum feature formed integrally with said shield, wherein said shield retention means in said shield retaining position urges said third datum feature to abut said first datum feature; and a fourth datum feature formed integrally with said shield, wherein said shield retention means in said shield retaining position urges said fourth datum feature to abut said second datum feature; a vacuum pump means operably connected to both a first pumping manifold and a second pumping manifold, wherein the first pumping manifold is configured to evacuate said vacuum chamber, and wherein the second pumping manifold is configured to evacuate said loading chamber when said retention stage lifting means is in said retention stage loading position.

In a related embodiment of the ion beam sample preparation apparatus, the shield retention stage further comprises a fifth datum feature, and the shield further comprises a sixth datum feature formed integrally with the shield, wherein the shield retention means in said shield retaining position urges said sixth datum feature to abut said fifth datum feature.

In a related embodiment of the ion beam sample preparation apparatus, the first shielding surface meets said proximal sample surface at an angle of less than about 90 degrees and more than about 80 degrees.

In a related embodiment of the ion beam sample preparation apparatus, the first shielding surface meets said proximal sample surface at an angle of less than about 87 degrees and more than about 83 degrees.

In a related embodiment of the ion beam sample preparation apparatus, the first shielding surface is made of non-magnetic material having low sputtering-yield.

In a related embodiment of the ion beam sample preparation apparatus, at least a portion of the first shielding surface is made of tantalum or titanium.

In a related embodiment of the ion beam sample preparation apparatus, the third datum feature is a datum surface and at least a portion of said datum surface is coextensive with at least a portion of said proximal sample surface.

In a related embodiment of the ion beam sample preparation, the proximal sample surface has at least one recessed portion configured for the flowing of adhesive between the shield and the sample.

In a related embodiment of the ion beam sample preparation apparatus, the shield further comprises a sample clamping means coupled to the shield and configured to hold the sample against said proximal sample surface.

In a related embodiment of the ion beam sample preparation apparatus, the shield further comprises: a second shielding surface having a portion disposed in the path of a portion of the ion beam; a shield edge formed where the first shielding surface meets the proximal sample surface; and a visible alignment mark on the second shielding surface, configured such that the location of said alignment mark is in a predetermined relationship to the region where the ion beam impinges on said shield edge when said shield is held in the shield retaining position of the shield retention means.

In a related embodiment of the ion beam sample preparation apparatus, the shield is made of a cladding material joined to a core material such that a portion of the cladding material forms at least a portion of the first shielding surface, and a portion of the core material forms the third and fourth datum features of the shield. In a related embodiment, the cladding material is a non-magnetic material having low sputtering-yield.

Another embodiment of the present disclosure is directed to an apparatus for ion beam sample preparation which comprises: an ion beam irradiating means disposed in a vacuum chamber and directing an ion beam toward a shield retention stage; the shield retention stage being disposed in the vacuum chamber; said shield retention stage comprising: a first datum feature; a second datum feature; a shield retention means having at least a shield releasing position and a shield retaining position; a retention stage lifting means coupled to said shield retention stage and configured to move said shield retention stage between a retention stage loading position and a retention stage processing position, characterized in that when the retention stage lifting means is in said retention stage loading position, a substantially vacuum-tight loading chamber is created between the shield retention stage and a portion of the vacuum chamber, and further characterized in that when the retention stage lifting means is in said retention stage loading position a substantially vacuum-tight seal is created between the loading chamber and the portion of the vacuum chamber in which the ion beam irradiating means is disposed; a lift drive coupled to said retention stage lifting means and operable to move said retention stage lifting means between said retention stage loading position and said retention stage processing position; a removable and replaceable chamber cover disposed to allow access to said loading chamber when said retention stage lifting means is held in said retention stage loading position, characterized in that said chamber cover provides a substantially vacuum-tight seal when in place on said vacuum chamber; a shield having at least a rigid planar portion, removably and replaceably held in said shield retention stage, said shield further comprising: a proximal sample surface configured to durably adhere the sample to the shield; a first shielding surface disposed in the path of the ion beam and positioned to shield a portion of the ion beam directed at the sample when said shield is held in the shield retaining position of the shield retention means and the retention stage lifting means is held in the retention stage processing position; a third datum feature formed integrally with said shield, wherein said shield retention means in said shield retaining position urges said third datum feature to abut in thermally conductive contact with said first datum feature; and a fourth datum feature formed integrally with said shield, wherein said shield retention means in said shield retaining position urges said fourth datum feature to abut said second datum feature; a vacuum pump means operably connected to both a first pumping manifold and a second pumping manifold, wherein the first pumping manifold is configured to evacuate said vacuum chamber, and wherein the second pumping manifold is configured to evacuate said loading chamber when said retention stage lifting means is in said retention stage loading position; a first thermal transfer member in thermally conductive contact with the shield retention stage; and a heat sink means configured to conduct heat away from said first thermal transfer member.

In a related embodiment of the ion beam sample preparation apparatus, the heat sink means is configured to use nitrogen to conduct heat away from the first thermal transfer member.

In a related embodiment of the ion beam sample preparation apparatus, the shield is made of a cladding material joined to a core material such that a portion of the cladding material forms at least a portion of the first shielding surface, and a portion of the core material forms the third and fourth datum features of the shield. In a related embodiment, the core material has high thermal conductivity. In a related embodiment the core material comprises copper.

Another embodiment of the present disclosure is directed to an apparatus for ion beam sample preparation which comprises: an ion beam irradiating means disposed in a vacuum chamber and directing an ion beam toward a shield retention stage; the shield retention stage being disposed in the vacuum chamber; said shield retention stage comprising: a first datum feature; a second datum feature; a shield retention means having at least a shield releasing position and a shield retaining position; a retention stage lifting means coupled to said shield retention stage and configured to move said shield retention stage between a retention stage loading position and a retention stage processing position, characterized in that when the retention stage lifting means is in said retention stage loading position, a substantially vacuum-tight loading chamber is created between the shield retention stage and a portion of the vacuum chamber, further characterized in that when the retention stage lifting means is in said retention stage loading position, a substantially vacuum-tight seal is created between the loading chamber and the portion of the vacuum chamber in which the ion beam irradiating means is disposed, and further characterized in that when the retention stage lifting means is in said retention stage loading position, said shield retention stage is in thermally conductive contact with a portion of said vacuum chamber; a lift drive coupled to said retention stage lifting means and operable to move said retention stage lifting means between said retention stage loading position and said retention stage processing position; a removable and replaceable chamber cover disposed to allow access to said loading chamber when said retention stage lifting means is held in said retention stage loading position, characterized in that said chamber cover provides a substantially vacuum-tight seal when in place on said vacuum chamber; a shield having at least a rigid planar portion, removably and replaceably held in said shield retention stage, said shield further comprising: a proximal sample surface, configured to durably adhere the sample to the shield; a first shielding surface, disposed in the path of the ion beam, and positioned to shield a portion of the ion beam directed at the sample when said shield is held in the shield retaining position of the shield retention means and the retention stage lifting means is held in the retention stage processing position; a third datum feature formed integrally with said shield, wherein said shield retention means in said shield retaining position urges said third datum feature to abut in thermally conductive contact said first datum feature; and a fourth datum feature, formed integrally with said shield, wherein said shield retention means in said shield retaining position urges said fourth datum feature to abut said second datum feature; a vacuum pump means operably connected to both a first pumping manifold and a second pumping manifold, wherein the first pumping manifold is configured to evacuate said vacuum chamber, and wherein the second pumping manifold is configured to evacuate said loading chamber when said retention stage lifting means is in said retention stage loading position; a thermal transfer member, disposed so that said thermal transfer member is in thermally conductive contact with the shield retention stage when said retention stage lifting means is held in said retention stage processing position, and further disposed so that said thermal transfer member is not in thermally conductive contact with the shield retention stage when said retention stage lifting means is held in said retention stage loading position; and a heat sink means configured to conduct heat away from said thermal transfer member.

BRIEF DESCRIPTION OF THE DRAWINGS

These and other features, aspects, and advantages of the present invention will become better understood with regard to the following description, appended claims, and accompanying drawings where:

FIG. 1A shows the apparatus in a retention stage loading position prior to loading a shield in the shield retention stage.

FIG. 1B shows the apparatus in a retention stage loading position after loading a shield in the shield retaining position.

FIG. 1C shows the apparatus in a sample loading position after loading a shield in the shield retention stage, and after the fitting of a chamber cover to the loading chamber.

FIG. 2 shows the apparatus in a retention stage processing position.

In FIG. 14A the shield retention stage lifting means is shown in a sample loading position and the shield retention means is shown in the shield retaining position.

In FIG. 14B the shield retention stage lifting means is shown in the sample processing position.

In FIG. 15A the shield retention stage lifting means is shown in a sample loading position and the shield retention means is shown in the shield retaining position.

In FIG. 15B the shield retention stage lifting means is shown in the sample processing position.

LIST OF REFERENCE NUMBERS APPEARING IN THE FIGURES

Figure 1A:
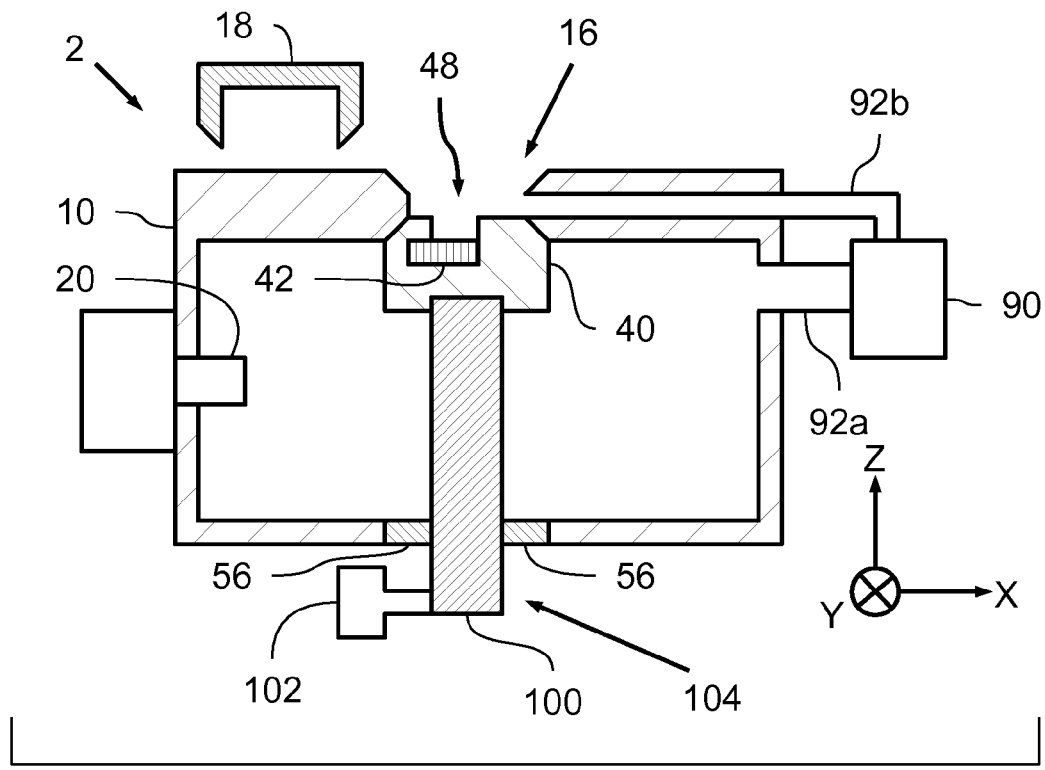
FIG. 1A shows a schematic cross-sectional view of an ion beam sample preparation apparatus, additionally comprising retention stage lifting means according to an embodiment of the present disclosure.

2—ion beam sample preparation apparatus
8—sample
10—vacuum chamber
16—loading chamber
18—chamber cover
20—ion beam irradiating means
22—central ion beam axis
40—shield retention stage
42—shield retention means
42a—shield retention means first member
42b—shield retention means second member
46—shield retaining position
48—shield releasing position
56—vacuum seal
60—shield
61—shielding surface
61a, 61b, etc.—first shielding surface, second shielding surface, etc.
62—proximal sample surface
63—shield edge
64—recessed portion
65—visible alignment mark
66—core material
67—cladding material
68—sample clamping means
70a, 70b, 70c, 70d, 70e, 70f—first datum feature, second datum feature, third datum feature, fourth datum feature, fifth datum feature, sixth datum feature.
72—datum surface
80—thermal transfer member
84—heat sink means
90—vacuum pump means
92—pumping manifold
92a, 92b, etc.—first pumping manifold, second pumping manifold etc.
100—retention stage lifting means
102—lift drive
104—retention stage loading position
106—retention stage processing position

DESCRIPTION

The Broad Ion Beam Slope-Cutting (BIBSC) sample preparation procedure can be described as a series of process steps, p1-p5:

p1) Aligning the desired region of the sample to be processed to a usable portion of an ion shield;

p2) Aligning the sample and shield in the BIBSC ion-milling system such that the desired region of the sample can be processed by the ion beam or beams;

p3) Evacuating the ion-milling system to vacuum levels appropriate for ion beam milling;

p4) Performing the ion-milling operation or operations, sometimes using a process monitoring step such as in situ light-microscopy imaging to verify sufficient cut depth and quality of the cross section;

p5) Venting of the BIBSC ion-milling equipment and removal of the sample from the equipment.

The analysis of prepared BIBSC sample can be described as a series of process steps, p6-p9:

p6) Introduction of the sample to the ultimate analysis microscope and initializing the microscope so that analysis can commence;

p7) Finding the location of the prepared cross-sectional surface by adjusting any number of the microscope's translation stages, tilt stages, and rotation stages so that the desired area can be imaged;

p8) Performing the desired microscopic or spectroscopic analyses;

p9) Removing the sample from the microscope;

p10) After analyzing the sample, a decision may be made to reprocess the sample to change the cut depth, position, or angle—traditionally requiring a repeat of p1-p9.

Embodiments of the present disclosure uniquely permit certain efficiencies and capabilities in the processing and subsequent observation and analysis of BIBSC produced samples. Beneficial features, functions, and aspects of the present disclosure include, but are not limited to:

1. Datum features on the shield, shield retention device in the sample-to-shield mounting apparatus, shield retention device in the BIBSC ion-mill, shield retention device in the ultimate analysis equipment allow significant time efficiencies in processing steps p1, p2 and p7;
2. The integral nature of the sample durably adhered to the shield, and to a lesser extent with the sample merely clamped to the shield, allows greater certainty in ensuring alignment of the shield to the sample remains consistent during p4 even over long time-scales and changes in temperature, whereas quality of the cross section cutting process is reduced if this precision alignment is not maintained;
3. The integral nature of the sample durably adhered to the shield in processing step p1 eliminates the requirement for expensive and sizable fixturing apparatus to maintain their spatial relationship together throughout the milling operation, and enables multiple samples to be prepared in advance of milling without multiple fixturing apparatus;
4. The integral nature of the sample durably adhered or clamped to the shield eliminates the requirement for dismounting the sample from the shield prior to observation in a microscope, even in cases where the smallest working distances between imaging objective and sample are employed. This permits reduction of both time and risk of damage to the sample during sample remounting in processing step p6;
5. In the case where reprocessing the sample as in step p10 is performed, the integral nature of the sample durably adhered or clamped to the shield can eliminate the need for steps p1 and p2 entirely, which significantly reduces processing time and risk of damage to the sample during sample remounting; and
6. In the case where reprocessing the sample as in step p10 is performed, the integral nature of the sample durably adhered or clamped to the shield allows different cross-sectional planes to be cut very close to the originally cut cross-sectional plane by varying the angle of ion beam impinging on the sample and shield.

Turning now to FIG. 1A, illustrated is a schematic cross-sectional view of an embodiment of an ion beam sample preparation apparatus 2. The embodiment of FIG. 1A is shown comprising: a vacuum chamber 10 in which a sample may be prepared by an ion beam irradiating means 20; a removable and replaceable chamber cover 18, which, when removed from chamber 10, allows access for sample and shield loading; a first pumping manifold 92a and a vacuum pump means 90, which together bring vacuum chamber 10 to vacuum levels appropriate for ion beam milling; a shield retention stage 40 and a shield retention means 42, the shield retention means 42 being shown in FIG. 1A in a shield releasing position 48; a retention stage lifting means 100, which is coupled to said shield retention stage 40; a lift drive 102 operably coupled to said retention stage lifting means 100 wherein the shield retention stage may be lifted into a retention stage loading position 104, and vacuum seal 56 which allows the retention stage lifting means to move up and down while maintaining vacuum seal between vacuum chamber 10 and the outside atmosphere. When shield retention stage 40 is raised to retention stage loading position 104, a loading chamber 16 is created. When in the retention stage loading position 104, vacuum sealing features of the shield retention stage 40 engage with vacuum sealing features of the vacuum chamber 10, and function to isolate said vacuum chamber from the outside atmosphere.

Figure 1B:
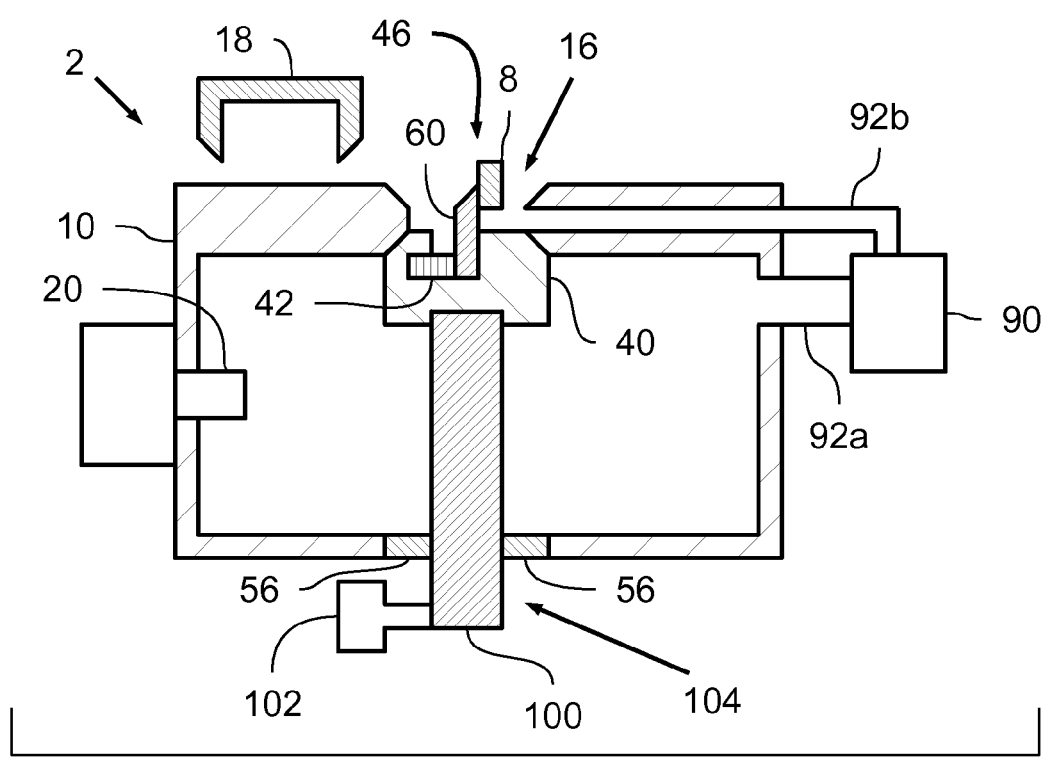
FIG. 1B shows a schematic cross-sectional view of an ion beam sample preparation apparatus, additionally comprising retention stage lifting means according to an embodiment of the present disclosure.

FIG. 1B shows the same embodiment as FIG. 1A, additionally showing a shield 60 with a sample 8 durably adhered to the shield has been placed in the shield retention stage 40 and is held in the stage by shield retention means 42 in a shield retaining position.

Figure 1C:
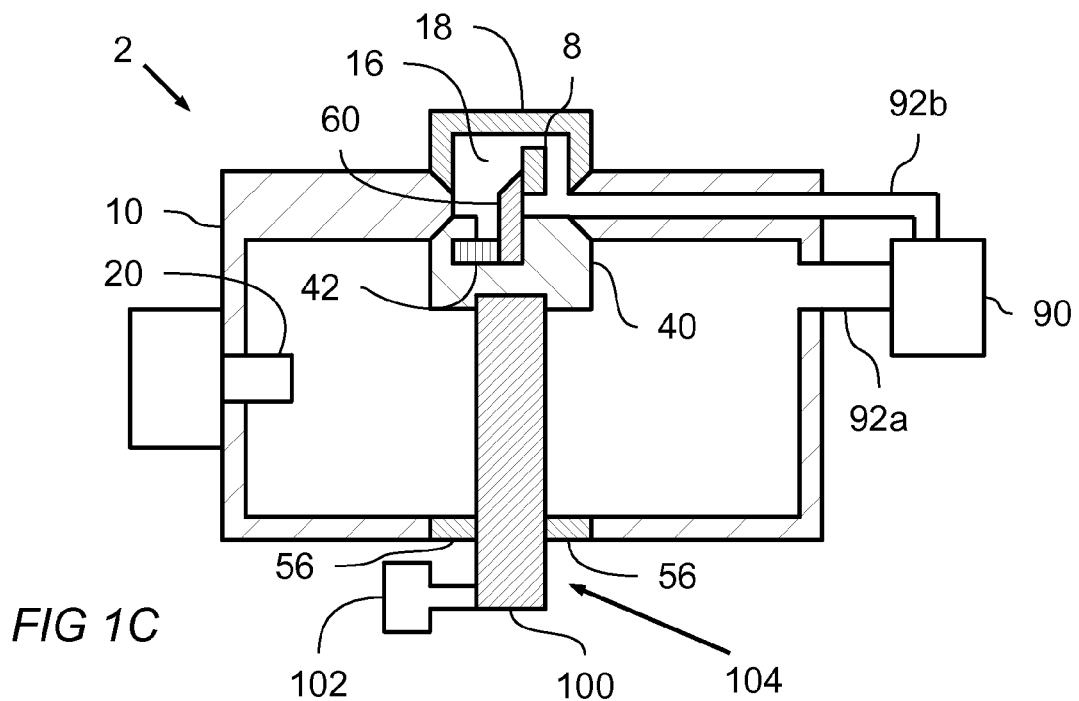
FIG. 1C shows a schematic cross-sectional view of an ion beam sample preparation apparatus, additionally comprising retention stage lifting means according to an embodiment of the present disclosure.

FIG. 1C shows the same embodiment as FIG. 1B, additionally showing that chamber cover 18 has been placed on vacuum chamber 10 to seal loading chamber 16 from the outside atmosphere. In a preferred embodiment, when chamber cover 18 is in place to seal the loading chamber from the outside atmosphere, the volume of loading chamber 16 is substantially smaller than the volume of vacuum chamber 10. When the apparatus is configured as in FIG. 1C, second pumping manifold 92b and pumping means 90 may be used to evacuate loading chamber 16 in preparation for lowering the shield retention stage into the retention stage processing position. When the loading chamber has been evacuated to suitable vacuum levels, the retention stage lifting means may be activated to lower the shield retention stage in preparation for ion beam milling of the sample.

Figure 2:
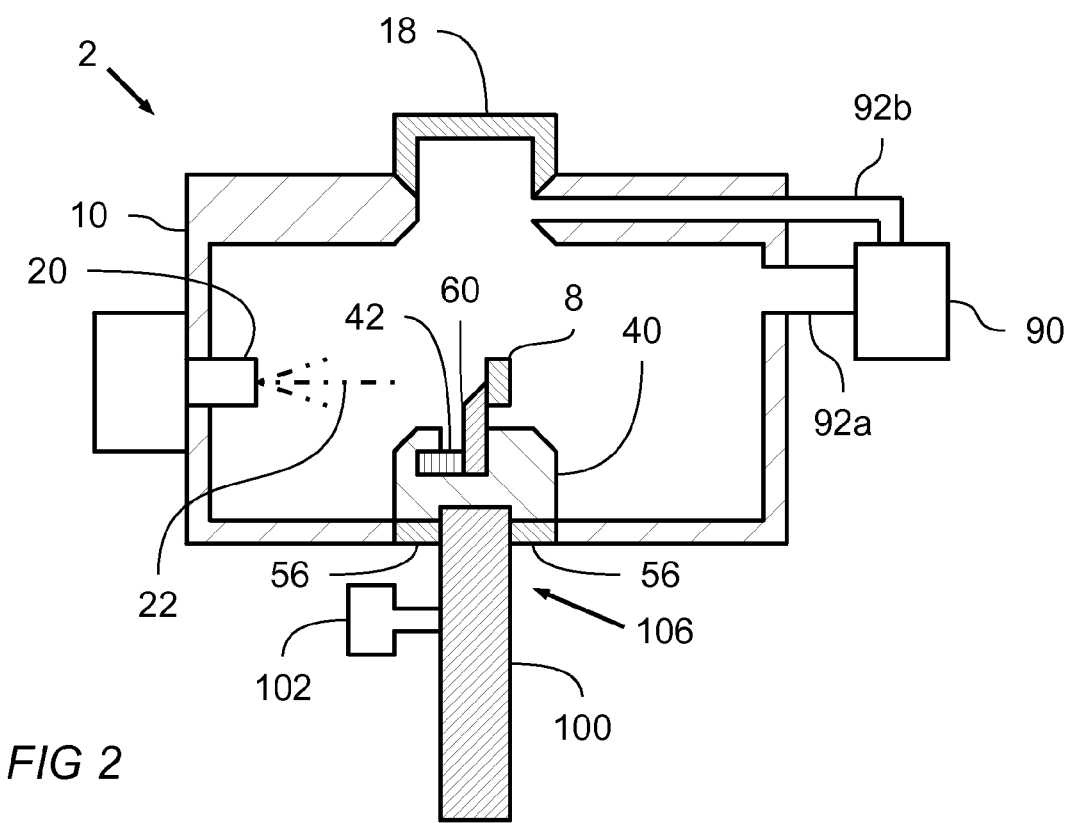
FIG. 2 shows a schematic cross-sectional view of an ion beam sample preparation apparatus, additionally comprising retention stage lifting means according to an embodiment of the present disclosure.

FIG. 2 shows the same embodiment as FIG. 1C. In FIG. 2 retention stage lifting means 100 and lift drive 102 have operated to lower the shield retention stage 40 into a retention stage processing position 106. The embodiment of FIG. 2 is shown comprising ion beam irradiating means 20, which directs an ion beam having a central ion beam axis 22 toward sample 8, and a shield 60, which shields at least a portion of sample 8 from at least a portion of the ion beam. After sample 8 has been prepared in the ion beam, the sequence of steps illustrated in FIG. 1A, FIG. 1B, FIG. 1C, and FIG. 2 may be reversed to raise the sample to the retention stage loading position, remove chamber cover 18, and remove the shield and sample combination for observation in a microscope.

With continuing reference to FIG. 2, the ion beam preferably comprises noble gas ions. Elements used for the ion beam may include, but are not limited to: Argon, Xenon, and Krypton. The ion beam may also comprise a mixture of ions and neutrals. When in retention stage processing position 106, the shield retention stage 40 is disposed in vacuum chamber 10 in a predetermined position and orientation with respect to central ion beam axis 22.

Figures 13A, 13B:
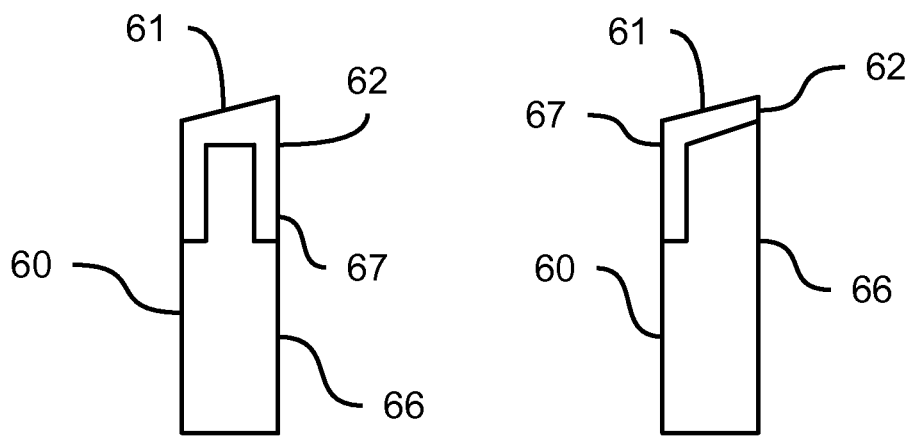
FIG. 13A and FIG. 13B show schematic views of embodiments of a shield comprising core material and cladding material.

In a preferred embodiment of shield 60, a material with good thermal conductivity may be used to improve thermal transfer between shield and the shield retention stage, said material including, but not limited to, a substantially non-magnetic metal. In another preferred embodiment of shield 60, a material with good thermal conductivity can be used as a core material 66 to improve thermal transfer between shield and the shield retention stage, and a substantially non-magnetic material with low sputtering-yield may be used as a cladding material 67 over the core material, whereby the cladding material forms at least part of the shielding surface 61 of shield 60. FIG. 13A and FIG. 13B illustrate two different embodiments of shield 60, wherein each embodiment is shown comprising a combination of core material 66 and cladding material 67.

Figure 3A:
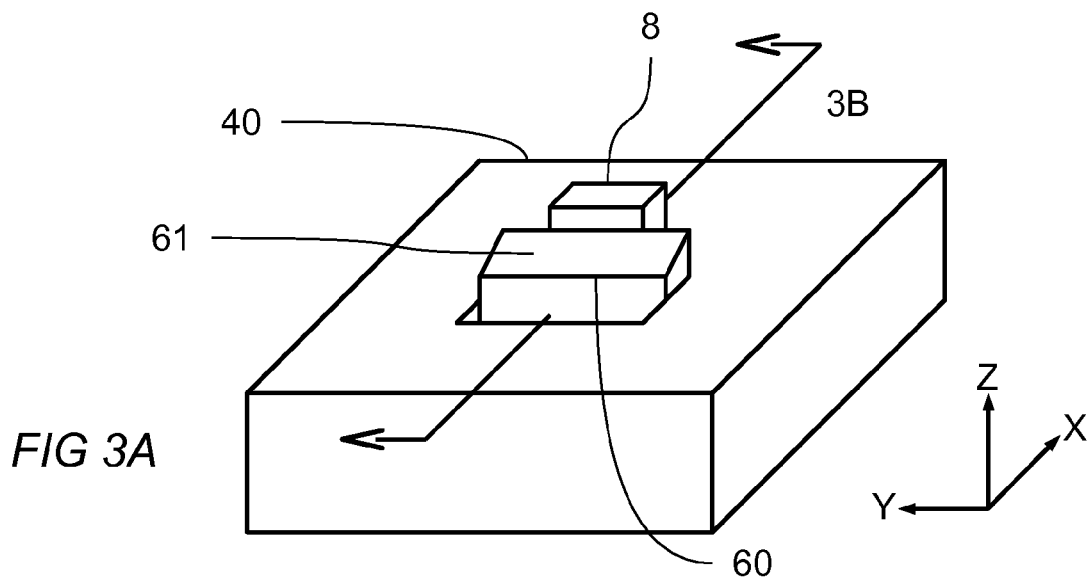
FIG. 3A shows a perspective view of a shield retention stage retaining a shield with a sample durably adhered to the shield. The figure also shows the cross section plane used for FIG. 3B.

FIG. 3A shows a perspective view of shield retention stage 40 on which sample 8 has been durably adhered to shield 60 prior to placing the shield and sample combination in a shield retaining position in shield retention stage 40. Shield 60 has a shielding surface 61, which is positioned in relation to sample 8 to shield at least a portion of said sample 8 from at least a portion of the ion beam. Also shown in FIG. 3A is a section line indicating the section view shown in FIG. 3B.

Figure 3B:
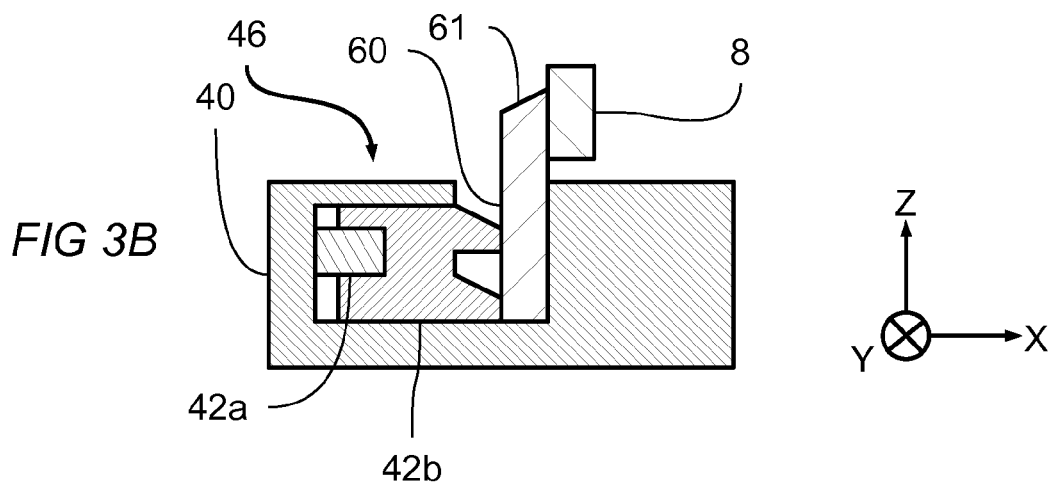
FIG. 3B shows a cross-sectional view of the shield retention stage of FIG. 3A with shield retention means in a shield retaining position.

FIG. 3B shows a section view illustrating the position and function of the shield retention means, which is part of shield retention stage 40. FIG. 3B shows an embodiment of the shield retention means in shield retaining position 46, the shield retention means comprising a shield retention means first member 42a and a shield retention means second member 42b. Shield retention means first member 42a urges shield retention means second member 42b against shield 60. The action of shield retention means first member also urges shield 60 against shield retention stage 40, and thereby maintains the position of shield 60 within shield retention stage 40 while the sample is prepared by ion beam. An embodiment of the shield retention means may comprise a spring for shield retention means first member 42a and a solid member as shield retention means second member 42b configured to slide within a cavity in shield retention stage 40.

Figure 4:
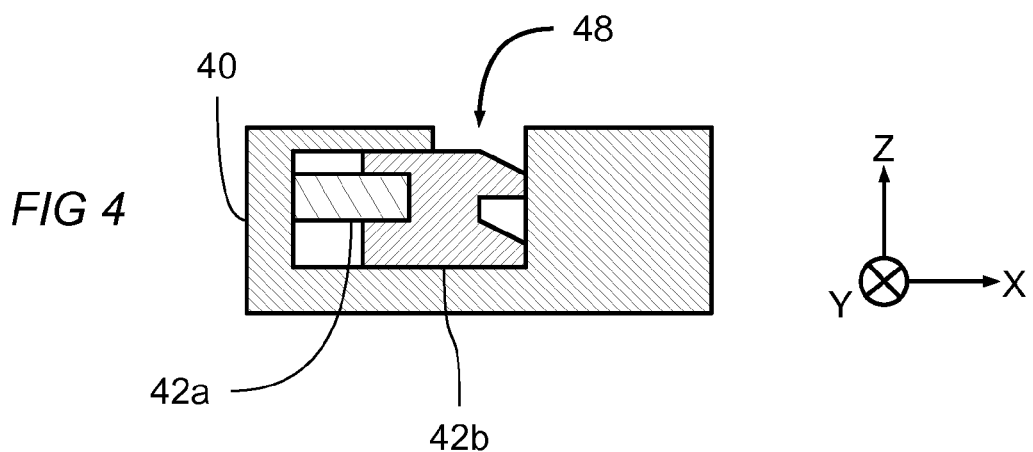
FIG. 4 shows a cross section similar to that of FIG. 3B, except that FIG. 4 shows the cross section with the shield retention means in a shield releasing position.

FIG. 4 shows a view from the same sectional plane as in FIG. 3B. However, in FIG. 4 the shield and sample have been removed to show a shield releasing position 48 of shield retention means. By means of the two positions provided by shield retention means, namely shield retaining position 46 as shown in FIG. 3A and FIG. 3B, and shield releasing position 48, as shown in FIG. 4, a shield may be removably and replaceably secured in shield retention stage 40. A sample that has been durably adhered to shield 60 may be processed, removed, and then reprocessed by simply placing it in the shield retaining position and preparing the sample again in the ion beam.

Figure 5A:
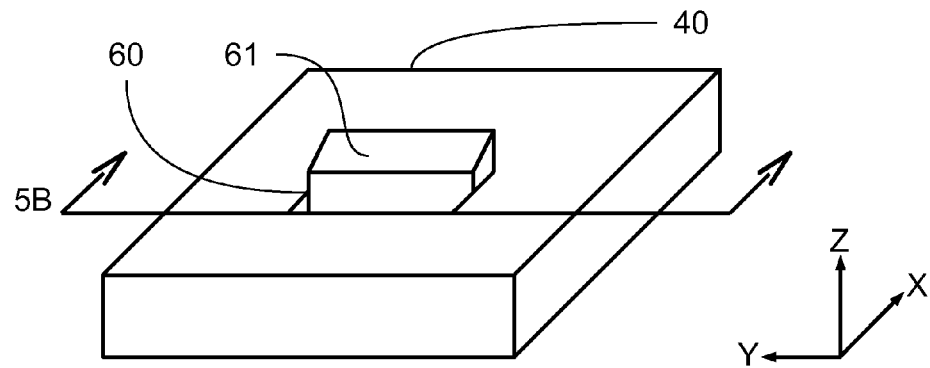
FIG. 5A shows a perspective view of a shield retention stage according to the present disclosure, indicating a cross-sectional plane for FIG. 5B.

FIG. 5A shows a perspective view of shield retention stage 40, on which shield 60 is retained, wherein said shield has a shielding surface 61. FIG. 5A also shows a sectional plane used for FIG. 5B.

Figure 5B:
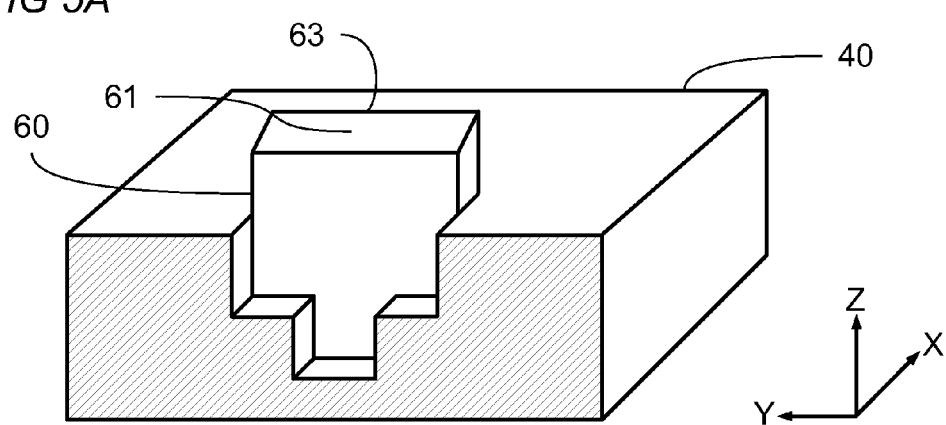
FIG. 5B shows a perspective sectional view of the shield retention stage of FIG. 5A, with the shield positioned in the shield retaining position.

FIG. 5B shows a sectional perspective view illustrating physical features of both shield 60 and shield retention stage 40, which facilitate accurate and repeatable positioning of the shield with respect to the shield retention stage. The positioning of shield 60 assures that shielding surface 61 and shield edge 63 are accurately positioned and accurately oriented with respect to the shield retention stage and are positioned with respect to central ion beam axis 22 to intercept at least a portion of the ion beam directed toward the sample.

Figure 6:
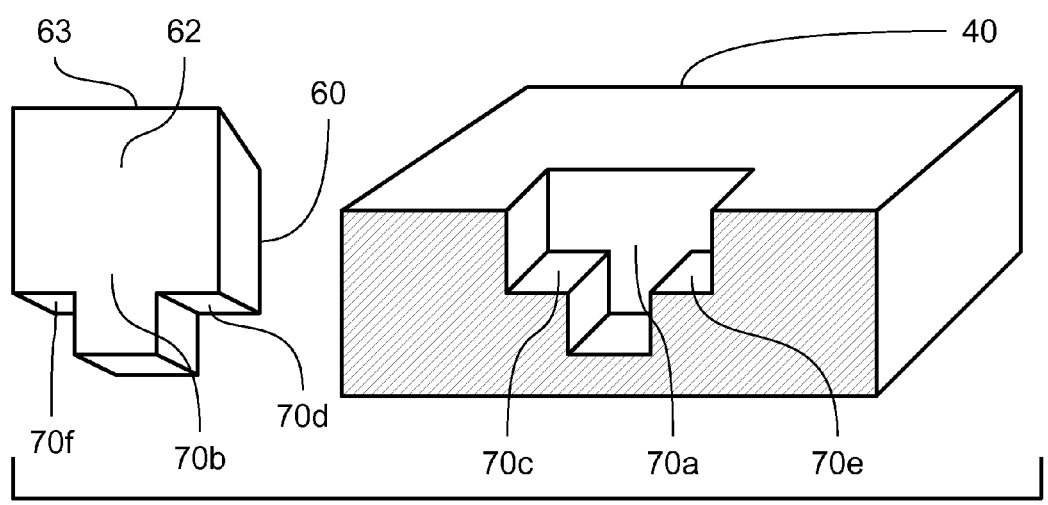
FIG. 6 shows an exploded perspective section view of the shield and shield retention stage of FIG. 5B. Datum features of both the shield and the shield retention stage are made visible in this view.

FIG. 6 shows a sectional perspective view as in FIG. 5B in which preferred embodiments of both shield 60 and shield retention stage 40 have a plurality of datum features 70a, 70b, 70c, 70d, 70e, and 70f. In the exploded view shown in FIG. 6, shield 60 has been removed from shield retention stage 40 and the shield is turned to expose a proximal sample surface 62 upon which a sample may be durably adhered prior to sample preparation by the ion beam. The plurality of datum features 70a, 70b, 70c, 70d, 70e, and 70f is provided on both shield 60 and shield retention stage 40 and the datum features enable accurate and repeatable positioning of the shield 60 with respect to the shield retention stage 40. Datum features 70b, 70d, and 70f on the shield are shaped and positioned such that when they are caused to abut complementary datum features 70a, 70c, and 70e on the shield retention stage the shield may be held in a predetermined position and a predetermined orientation with respect to the central ion beam axis 22. Shield retention means 42 assures that datum features 70b, 70d, and 70f of shield 60 abut the corresponding datum features 70a, 70c, and 70e of the shield retention stage 40 when the shield is held in the shield retaining position. Shield edge 63, also visible in FIG. 6, is also caused to be in a predetermined position and predetermined orientation when the shield is held in the shield retaining position.

Datum features are arranged in pairs such that a datum feature on the shield has a corresponding datum feature on the shield retention stage. In FIG. 6 one such pair of datum features is datum feature 70a on the shield retention stage and datum feature 70b on the shield. Another pair of datum features shown in FIG. 6 is datum feature 70c on the shield retention stage and datum feature 70d on the shield. Another pair of datum features shown in FIG. 6 is datum feature 70e on the shield retention stage and datum feature 70f on the shield. When the shield is in the shield retaining position, the shield retention means acts to urge the pairs of datum features to abut, thereby constraining the position of the shield with respect to the position of the shield retention stage. Datum features may be datum surfaces, as is shown in the preferred embodiment of FIG. 6, or they may be datum edges, datum vertices, or combinations of datum surfaces, datum edges, and datum vertices.

Turning now to FIG. 7A, FIG. 7B, FIG. 8A, FIG. 8B, FIG. 9, and FIG. 10, shown are various features and embodiments of shield 60 according to the present disclosure.

Figure 7A:
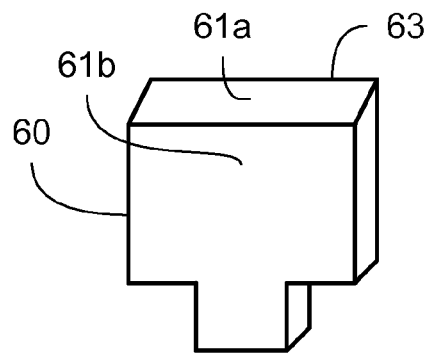
FIGS. 7A and 7B show perspective views of a shield according to embodiments of the present disclosure, viewed from the ion beam side of the shield.

FIG. 7A is a perspective view of a shield showing a first shielding surface 61a, a second shielding surface 61b, and shield edge 63. Ions from the ion beam irradiating means that are blocked by the shield, and, in particular, the ions that are blocked by first shielding surface 61a are prevented from milling the sample. Ions not blocked by the shield may be used to prepare the sample for observation and analysis. When the ion beam is operating, ions may or may not impact second shielding surface 61b. Whether ions do impact second shielding surface 61b depends on a number a factors including, but not limited to: the size of the ion beam; the angle at which the ion beam is directed; and the position at which the ion beam is directed. It is a preferred embodiment of the shield that second shielding surface 61b be made of the same material as first shielding surface 61a. In preferred embodiments shield 60 is a generally planar rigid member, having one or more shielding surfaces that are smooth and may be polished, having a datum surface and at least an additional datum feature for facilitating accurate placement within the shield retention stage. Preferred materials for the shield are non-magnetic metals with low sputter yield including, but not limited to, tantalum or titanium. Lower cost embodiments of shield 60 may comprise core material 66 for the majority of the shield and cladding material 67 used for the shielding surfaces. Preferred core materials include, but are not limited to, copper. Preferred cladding materials include, but are not limited to, tantalum or titanium. FIG. 13A and FIG. 13B illustrate two different embodiments of a shield 60, wherein each embodiment is shown comprising a combination of core material 66 and cladding material 67.

Figure 7B:
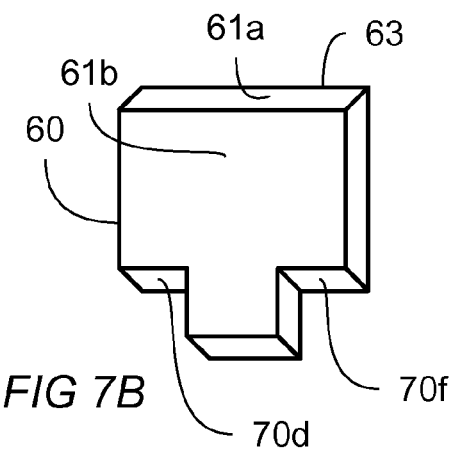

FIG. 7B shows the same shield as shown in FIG. 7A, but from a different angle, thereby illustrating the position and nature of a plurality of datum features 70d and 70f.

Figure 8A:
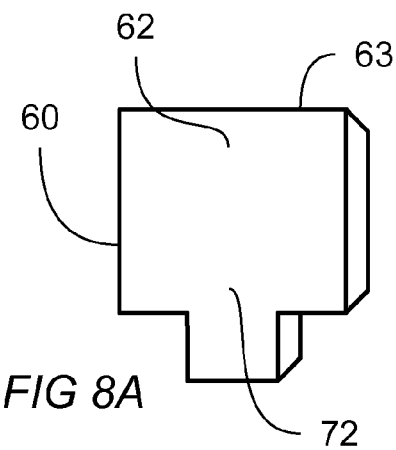
FIGS. 8A and 8B show perspective views of a shield according to embodiments of the present disclosure, viewed from the proximal sample side of the shield.

FIG. 8A shows the same shield as shown in FIG. 7A and FIG. 7B. FIG. 8A shows a perspective view of shield 60 from the side of the shield closest to the sample during ion beam sample preparation. Proximal sample surface 62 may be used to adhere the sample material to be prepared in the apparatus. Datum surface 72 is a datum feature that is a surface. In a preferred embodiment, at least a portion of proximal sample surface 62 may be coextensive with at least a portion of datum surface 72. Shield edge 63 is formed by the intersection of first shielding surface 61a and proximal sample surface 62. The angle between first shielding surface 61a and proximal sample surface 62 has an impact on the quality of milling performed on the sample by the ion beam. A preferred embodiment is achieved when said first shielding surface 61*a* meets said proximal sample surface 62 at an angle of less than about 90 degrees and more than about 80 degrees. An even more preferred embodiment is achieved when said first shielding surface 61*a* meets said proximal sample surface 62 at an angle of less than about 87 degrees and more than about 83 degrees.

Figure 8B:
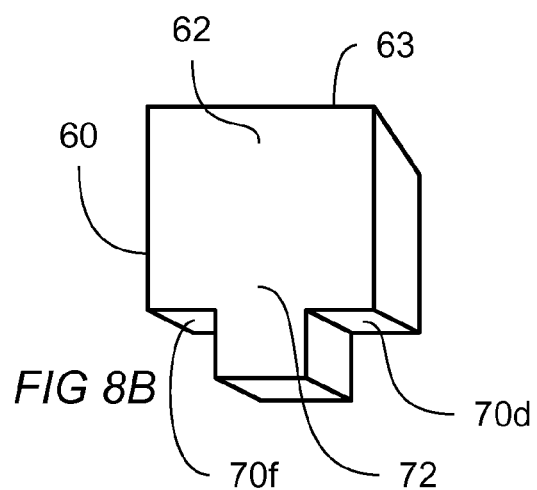

FIG. 8B shows the same shield as shown in FIG. 8A, but from a different angle, thereby illustrating the position and nature of a plurality of datum features 70*d* and 70*f*, and datum surface 72, present on shield 60.

Figure 9:
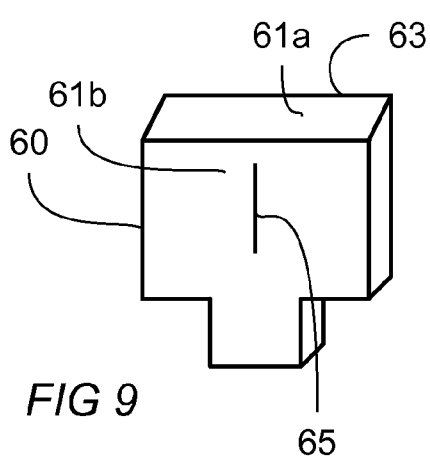
FIG. 9 shows a perspective view of another shield according to the present disclosure, viewed from the ion beam side of the shield and having a visible alignment feature.

FIG. 9 shows a perspective view of shield 60 having first shielding surface 61*a*, second shielding surface 61*b*, shield edge 63, and additionally comprising a visible alignment mark 65. When the shield is held in the shield retaining position, the visible alignment mark is positioned so that it indicates the approximate location where a portion of the ion beam will pass over shield edge 63 and impact the sample when the shield edge is substantially perpendicular to the central ion beam axis.

Figure 10:
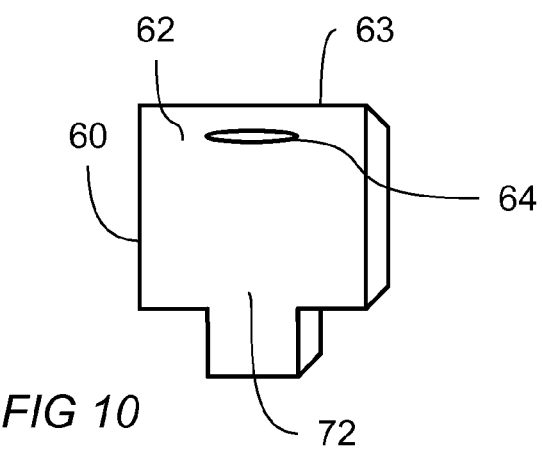
FIG. 10 shows a perspective view of another shield according to the present disclosure, viewed from the proximal sample side of the shield and having a recessed portion to facilitate the flow of adhesive under the sample.

FIG. 10 shows a perspective view of shield 60 from the side of the shield closest to the sample during ion beam sample preparation. Proximal sample surface 62 may be used to adhere the sample material to the shield prior to ion beam sample preparation in the apparatus. Recessed portion 64 provides a recessed portion of proximal sample surface 62 useful for flowing adhesive under the sample, thereby facilitating the durable adhering of sample to shield. Preferred materials used to adhere the sample to the shield include, but are not limited to: UV cured glue, light cured glue, superglue, silver paint, and wax.

Figure 11A:
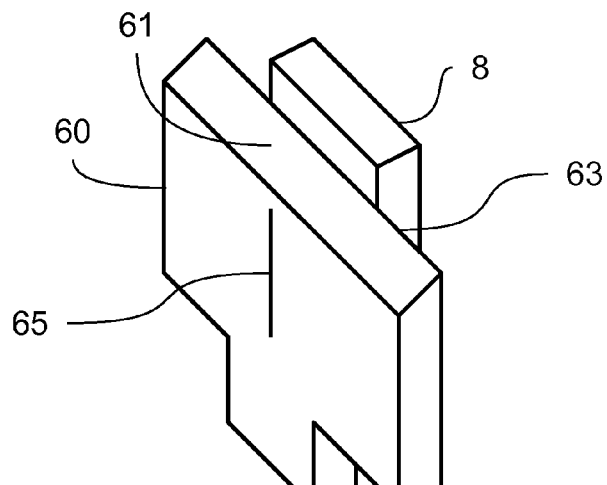
FIGS. 11A and 11B show perspective views of a shield with a durably adhered sample, both before (FIG. 11A) and after (FIG. 11B) preparation in an ion beam sample preparation thermal management apparatus according to the present disclosure.
Figure 11B:
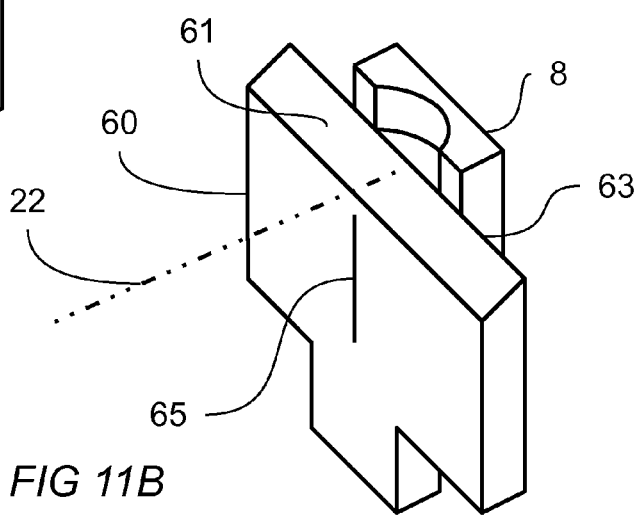

Turning now to FIG. 11A, shown is a perspective view of shield 60, shielding surface 61, sample 8 durably adhered to the shield, and visible alignment mark 65. FIG. 11A depicts the sample prior to ion beam preparation. FIG. 11B is a perspective view of the same objects depicted in FIG. 11A. However, FIG. 11B represents the sample after ion beam sample preparation. Shielding surface 61 intercepts a portion of the ion beam, which travels along central ion beam axis 22. A portion of sample 8 is sputtered away by the ion beam during sample preparation, thereby exposing a portion of the sample lying in the plane defined by shield edge 63 and central ion beam axis 22. A sample prepared in this way will be suitable for observation or analysis with a variety of microscopic or spectroscopic techniques, particularly those requiring a highly polished planar surface.

Figure 12A:
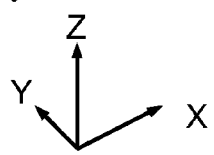
FIGS. 12A and 12B show an embodiment of a shield with integrated sample clamping means, according to an embodiment of the present disclosure.
Figure 12A:
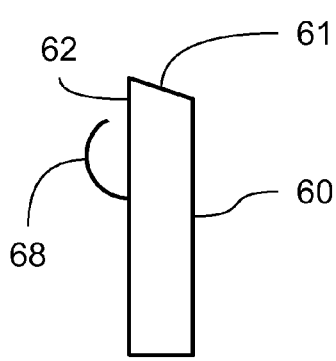
Figure 12B:
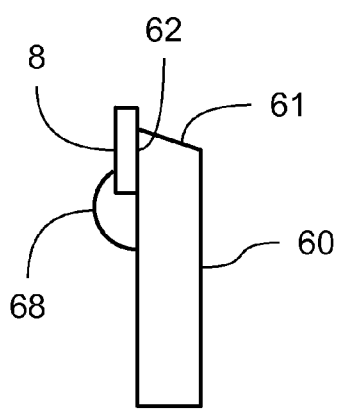

FIG. 12A and FIG. 12B illustrate another embodiment of shield 60, in which a sample clamping means 68 is formed integrally with the shield on the proximal sample surface 62. FIG. 12A depicts this shield prior to clamping a sample, while FIG. 12B depicts this shield after sample 8 has been secured to the shield by means of sample clamping means 68. In another embodiment, sample clamping means 68 may be formed separately and then coupled to the shield prior to clamping the sample. Adhesive may be applied between the sample clamping means and the sample to further ensure the sample does not move with respect to the shield.

Use of the apparatus shown in FIG. 1A, FIG. 1B, FIG. 1C, and FIG. 2 may proceed with reference to the following steps. Outside of the vacuum chamber, a sample may be durably adhered to a shield. The shield retention stage may be moved to the retention stage loading position, thereby creating a loading chamber that is vacuum-tight with respect to the portion of the vacuum chamber in which the ion beam irradiating means is disposed. Then the loading chamber may be pressurized to atmospheric pressure by operation of the vacuum pump means through the second pumping manifold. The chamber cover may then be removed. With the chamber cover removed, the shield and sample combination may be secured in the shield retaining position of the shield retention stage. The chamber cover may then be replaced. With the chamber cover in place on the vacuum chamber the vacuum pump means may be operated to evacuate the loading chamber through the second pumping manifold thereby obtaining vacuum levels substantially below atmospheric pressure. The retention stage lifting means and lift drive may then be operated to move the shield retention stage to the retention stage processing position. The vacuum pump means may operate throughout the loading process through the first pumping manifold to maintain vacuum levels in the vacuum chamber. Once the sample and shield have been moved into the retention stage processing position, the ion beam irradiating means may then be operated to prepare the sample. When the sample has been prepared to the extent desired by the user of the apparatus, the ion beam irradiating means may be turned off. Then the retention stage lifting means and lift drive may operate to move the shield retention stage back to the retention stage loading position. With the vacuum tight loading chamber having been created again, the loading chamber may be pressurized to atmospheric pressure without disturbing the vacuum in the remainder of the vacuum chamber. The chamber cover may be removed, and the prepared sample may be removed from the apparatus along with the shield to which it was previously adhered. A microscope may be fitted with a shield retention stage so that the prepared sample and shield may be retained and thereby the prepared region of the sample may be observed in the microscope. After observation, the user may decide that additional sample preparation is needed. Since the sample is still durably adhered to the shield, it is a simple matter to return the sample and shield to the vacuum chamber for additional processing. The datum features on both the shield and the shield retention stage ensure that the shield may be retained in substantially the same position and orientation each time the sample is processed in the apparatus. A kit comprising a shield retention stage 40 with a plurality of datum features 70*a*, 70*c*, and 70*e*, shield retention means 42, and at least one shield 60 with a plurality of datum features 70*b*, 70*d*, and 70*f* may be supplied for fitting to a microscope. Such a kit facilitates the microscopic observation of samples prepared in the ion beam sample preparation apparatus 2.

Figure 14A:
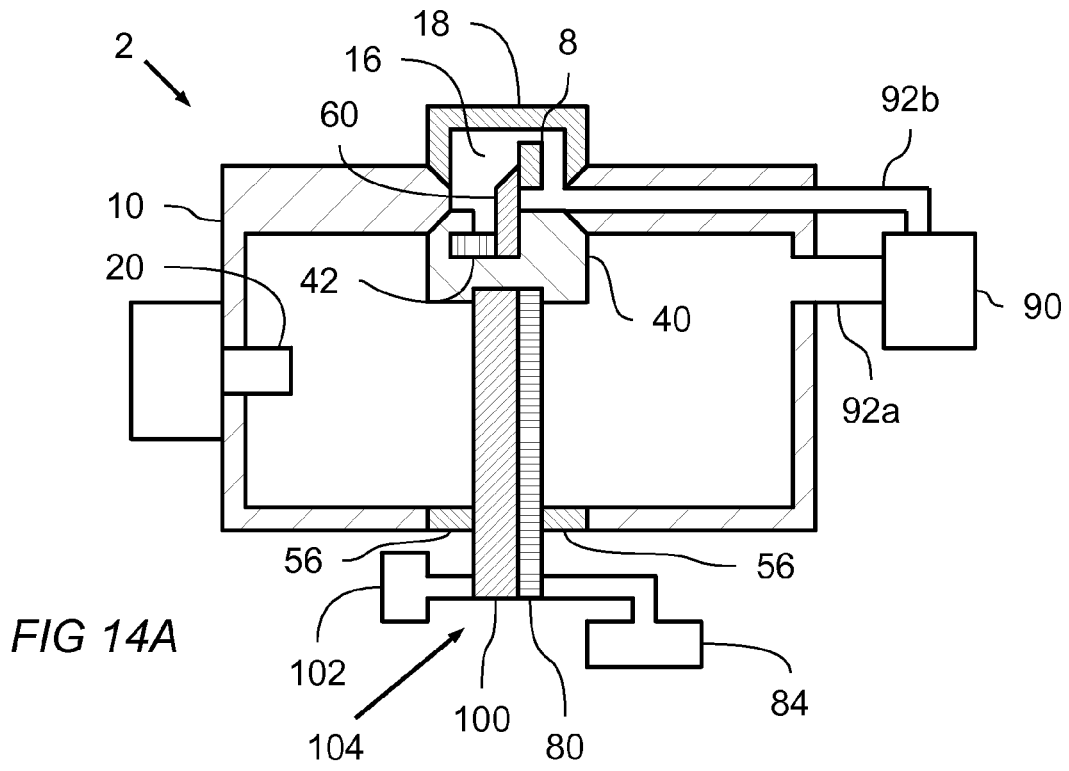
FIG. 14A shows a schematic cross-sectional view of an ion beam sample preparation apparatus, having both a shield retention stage lifting means and a heat sink means for temperature control of the sample.

Turning now to FIG. 14A, illustrated is a schematic cross-sectional view of an embodiment of an ion beam sample preparation apparatus 2 adapted to control the temperature of shield retention stage 40. The embodiment of FIG. 14A is shown comprising: a vacuum chamber 10 in which a sample may be prepared by an ion beam irradiating means 20; a removable and replaceable chamber cover 18, which, when removed from chamber 10, allows access for sample and shield loading; a first pumping manifold 92*a* and a pumping means 90, which together bring vacuum chamber 10 to vacuum levels appropriate for ion beam milling; a shield retention stage 40 and a shield retention means 42, the shield retention means 42 being shown in FIG. 14A in a shield retaining position; a retention stage lifting means 100 which is coupled to said shield retention stage 40; a lift drive 102 operably coupled to said retention stage lifting means 100, wherein the shield retention stage may be moved between a retention stage loading position 104 as shown in FIG. 14A and a retention stage processing position 106 as shown in FIG. 14B, and vacuum seal 56, which allows the retention stage lifting means to move up and down while maintaining vacuum seal between vacuum chamber 10 and the outside atmosphere.

The apparatus of FIG. 14A is shown further comprising: a thermal transfer member 80, which is in thermally conductive contact with shield retention stage 40, and heat sink means 84, which facilitates heat exchange between thermal transfer member 80 and a heat exchange fluid or gas. When shield retention means 42 is in the shield retaining position, it urges thermally conductive contact between shield 60 and shield retention stage 40, thereby facilitating heat exchange between shield and shield retention stage. When shield retention stage 40 is raised to retention stage loading position 104 a loading chamber 16 is created. When in the retention stage loading position 104, vacuum sealing features of the shield retention stage 40 engage with vacuum sealing features of the vacuum chamber 10 and function to isolate said vacuum chamber from the outside atmosphere. Second pumping manifold 92b and pumping means 90 may be used to evacuate loading chamber 16 in preparation for lowering the shield retention stage into the retention stage processing position. In a preferred embodiment, when chamber cover 18 is in place to seal the loading chamber from the outside atmosphere, the volume of loading chamber 16 is substantially smaller than the volume of vacuum chamber 10.

With continuing reference to FIG. 14A, the ion beam preferably comprises noble gas ions. Elements used for the ion beam may include but are not limited to: Argon, Xenon, and Krypton. The ion beam may also comprise a mixture of ions and neutrals. Heat sink means 84 may use gaseous nitrogen, liquid nitrogen, other gases, or other liquids as a heat absorbing medium. Heat sink means 84 may additionally comprise temperature control means capable of substantially maintaining thermal transfer member 80 at a predetermined temperature. Shield retention stage 40 of FIG. 14A and FIG. 14B has the same features and functions possessed by shield retention stage 40 shown in FIG. 1A, FIG. 1B, FIG. 1C, FIG. 2, FIG. 3A, FIG. 3B, FIG. 4, FIG. 5A, FIG. 5B, and FIG. 6. In addition, shield 60 of FIG. 14A and FIG. 14B has the same features, functions, and aspects possessed by shield 60 shown in FIG. 3A, FIG. 3B, FIG. 5A, FIG. 5B, FIG. 6, FIG. 7A, FIG. 7B, FIG. 8A, and FIG. 8B. In a preferred embodiment of shield 60, a material with good thermal conductivity can be used to improve thermal transfer between shield and the shield retention stage, said material including, but not limited to, a substantially non-magnetic metal. FIG. 13A and FIG. 13B show other preferred embodiments of shield 60 in which a material with good thermal conductivity can be used as a core material to improve thermal transfer between shield and the shield retention stage, and a substantially non-magnetic material with low sputtering-yield may be used as a cladding material over the core material, whereby the cladding material forms at least part of the shielding surface 61 of shield 60.

Figure 14B:
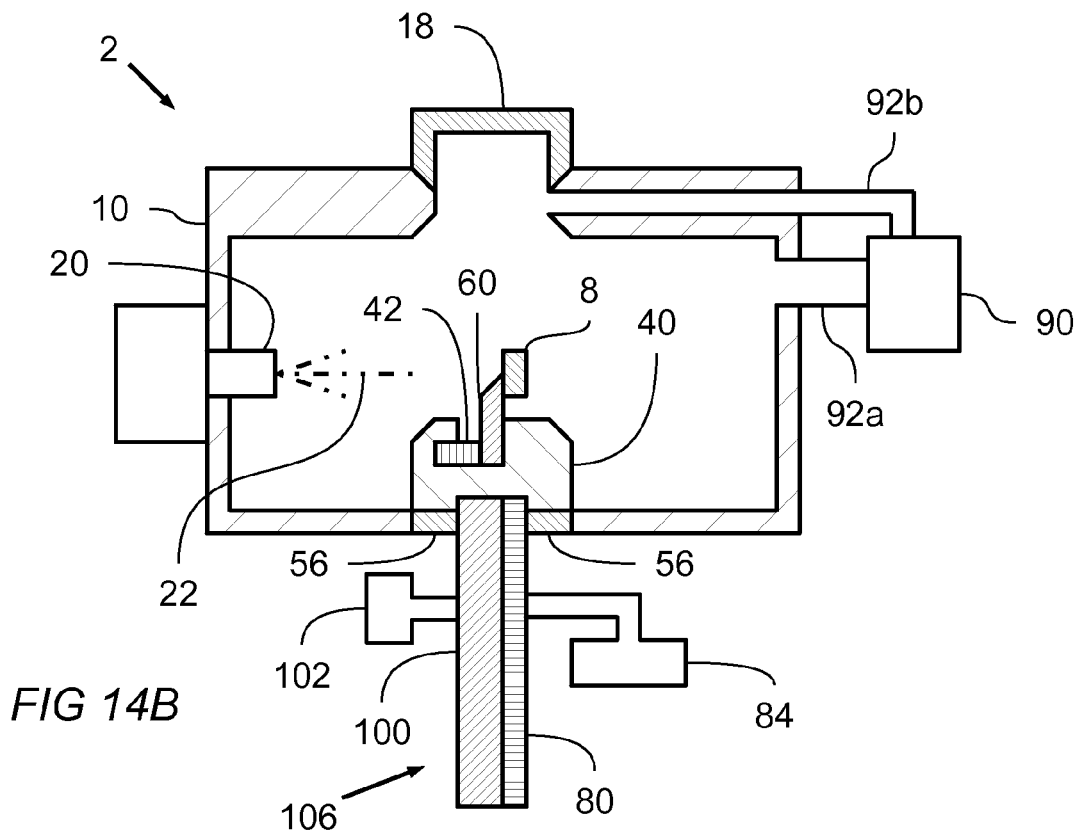
FIG. 14B shows a schematic cross-sectional view of the same apparatus as in FIG. 14A.

The apparatus of FIG. 14B shows the same apparatus as FIG. 14A. However, in FIG. 14B the retention stage lifting means 104 and lift drive 102 have operated to move shield retention stage 40 into retention stage processing position 106. When in the retention stage processing position, shield retention stage 40 is disposed in vacuum chamber 10 in a predetermined position and orientation with respect to central ion beam axis 22.

In the apparatus of FIG. 14A and FIG. 14B, the shield retention stage 40 datum features allow the interchangeable use of shield 60 previously described. By means of the two positions provided by the shield retention means, namely shield retaining position 46 as shown in FIG. 3B, and shield releasing position 48 as shown in FIG. 4, a shield may be removable and replaceably secured in shield retention stage 40. A sample that has been durably adhered to shield 60 may be processed, removed, and then reprocessed by simply placing it in the shield retaining position and preparing the sample again in the ion beam. The datum features on both shield and shield retention stage assure that the shield may be positioned in a substantially identical position and orientation multiple times.

Use of the apparatus of FIG. 14A and FIG. 14B may proceed according to all of the steps disclosed for the use of the apparatus of FIG. 1A, FIG. 1B, FIG. 1C, and FIG. 2. However, the thermal transfer member and heat sink means shown in the embodiment of FIG. 14A and FIG. 14B give the user additional capabilities. In the embodiment of FIG. 14A and FIG. 14B the thermal control works particularly well in concert with the retention stage lifting means, lift drive, and isolated loading chamber that is created when in the retention stage loading position. It may be the case that a sample is prepared in the ion beam while the sample is held at low temperature. Such a temperature may be below the dew point of the local atmosphere immediately outside of the apparatus. If the shield retention stage is at a temperature below the local dew point, then exposing it to the atmosphere during loading and unloading may result in water condensation in the loading chamber. Such water condensation would spoil the vacuum conditions maintained in the vacuum chamber if the wet retention stage were moved into the vacuum chamber. In addition, condensation, if allowed to form on the sample, may ruin the sample. The heat sink means may be beneficially used to bring the temperature of the shield retention stage above the local dew point before the user takes the chamber cover off to access the shield retention stage. The retention stage lifting means creates another benefit in that the creation of the loading chamber significantly reduces the volume of the apparatus that must be exposed to the ambient atmosphere during sample loading and unloading. This is a tremendous time saver whenever the temperature of the shield retention stage must be raised or lowered to match the ambient atmospheric temperature.

Figure 15A:
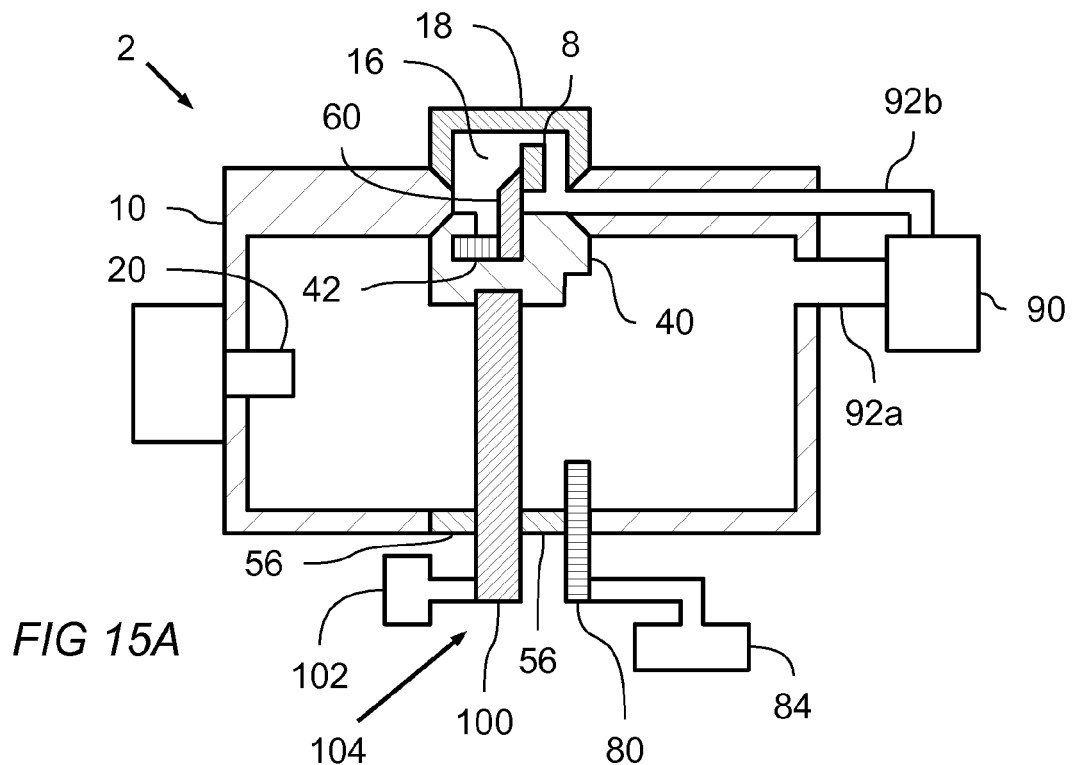
FIG. 15A shows a schematic cross-sectional view of another embodiment of an ion beam sample preparation apparatus, having both a shield retention stage lifting means and a heat sink means for temperature control of the sample.
Figure 15B:
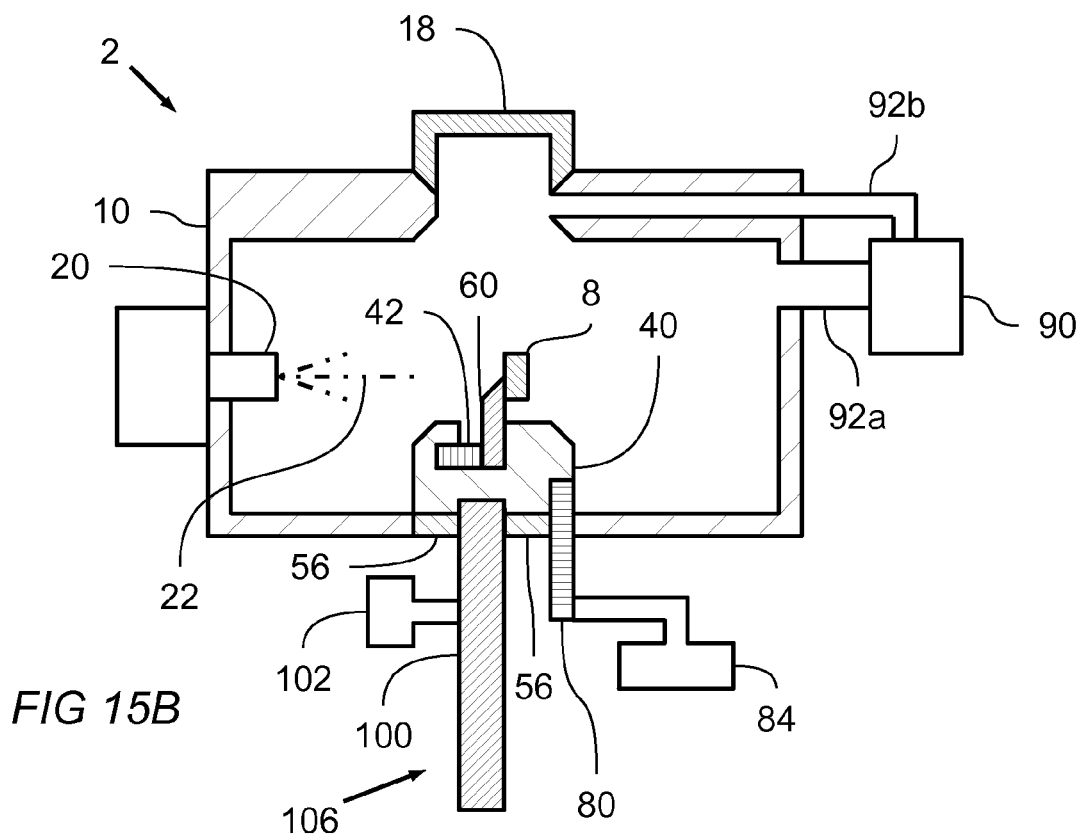
FIG. 15B shows a schematic cross-sectional view of the same apparatus as in FIG. 15A.

Turning now to FIG. 15A and FIG. 15B, illustrated is a schematic cross-sectional view of another embodiment of an ion beam sample preparation apparatus 2. The apparatus of FIG. 15A and FIG. 15B is adapted to control the temperature of shield retention stage 40 by means of a different configuration than the embodiment of FIGS. 14A and 14B. The embodiment of FIG. 15A is shown comprising: a vacuum chamber 10, in which a sample may be prepared by an ion beam irradiating means 20; a removable and replaceable chamber cover 18, which, when removed from chamber 10, allows access for sample and shield loading; a first pumping manifold 92a and a pumping means 90, which together bring vacuum chamber 10 to vacuum levels appropriate for ion beam milling; a shield retention stage 40 and a shield retention means 42, the shield retention means 42 being shown in FIG. 15A in a shield retaining position; a retention stage lifting means 100, which is coupled to said shield retention stage 40; a lift drive 102, operably coupled to said retention stage lifting means 100, wherein the shield retention stage may be moved between a retention stage loading position 104, as shown in FIG. 15A, and a retention stage processing position 106, as shown in FIG. 15B, and vacuum seal 56, which allows the retention stage lifting means to move up and down while maintaining vacuum seal between vacuum chamber 10 and the outside atmosphere. When shield retention stage 40 is raised to retention stage loading position 104, a loading chamber 16 is created. The apparatus of FIG. 15A and FIG. 15B is shown further comprising a thermal transfer member 80 and a heat sink means 84, which together facilitate heat exchange between thermal transfer member 80 and heat sink means 84.

The apparatus of both FIG. 15A and FIG. 15B are shown with a sample 8 durably adhered to a shield 60. The sample and shield combination are shown held in a shield retaining position of the shield retention means 42. Shield retention stage 40 and shield 60 work in the same way and have the same features and aspects as the shield retention stage and shield shown in FIG. 1A, FIG. 1B, FIG. 1C, FIG. 2, FIG. 3A, FIG. 3B, FIG. 4, FIG. 5A, FIG. 5B, FIG. 6, FIG. 7A, FIG. 7B, FIG. 8A, FIG. 8B, all previously described in the present disclosure. The shield retention stage of FIG. 15A and FIG. 15B has additional features that allow it to engage, in thermally conductive contact, with thermal transfer member 80 when the retention stage lifting means is in retention stage processing position 106. Also, the shield retention stage of FIG. 15A and FIG. 15B has features that allow it to disengage from thermally conductive contact with thermal transfer member 80 when the retention stage lifting means 100 is in retention stage loading position 104.

With continuing reference to FIG. 15A and FIG. 15B, when shield retention means 42 is in the shield retaining position, it urges thermally conductive contact between shield 60 and shield retention stage 40, thereby facilitating heat exchange between shield and shield retention stage. When retention stage lifting means is in the retention stage loading position 104 there is no thermally conductive contact between shield retention stage 40 and thermal transfer member 80. Furthermore, when in retention stage loading position 104, the shield retention stage may be in thermally conductive contact with a portion of vacuum chamber 10. Thermally conductive contact may allow the shield retention stage to exchange heat with the contacting portion of the vacuum chamber and thereby the sample, shield, and shield retention stage may approach the same temperature as exists in the contacting portion of the vacuum chamber.

When in the retention stage loading position 104, vacuum sealing features of the shield retention stage 40 engage with vacuum sealing features of the vacuum chamber 10 and function to isolate said vacuum chamber from the outside atmosphere. Second pumping manifold 92b and pumping means 90 may be used to evacuate loading chamber 16 in preparation for lowering the shield retention stage into the retention stage processing position. In a preferred embodiment, when chamber cover 18 is in place to seal the loading chamber from the outside atmosphere, the volume of loading chamber 16 is substantially smaller than the volume of vacuum chamber 10.

FIG. 15B shows the apparatus of FIG. 15A after the retention stage lifting means 100 and lift drive 102 have operated to move to the retention stage processing position 106. In this position, thermal transfer member 80 is in thermally conductive contact with shield retention stage 40. Heat sink means 84 may operate in this position to exchange heat through thermal transfer member 80, and thereby affect the temperature of shield retention stage 40. The thermally conductive contact established between shield 60 and shield retention stage 40 when the shield is held in the shield retaining position completes the thermal circuit and allows for the exchange of heat between heat sink means 84 and shield 60. In preferred embodiments, heat sink means 84 may use gaseous or liquid nitrogen as a heat exchange medium.

Use of the apparatus of FIG. 15A and FIG. 15B may proceed according to all of the steps disclosed for the use of the apparatus of FIG. 1A, FIG. 1B, FIG. 1C, and FIG. 2. However, the thermal transfer member and heat sink means shown in the embodiment of FIG. 15A and FIG. 15B give the user additional capabilities. In the embodiment of FIG. 15A and FIG. 15B the thermal control works particularly well in concert with the retention stage lifting means, lift drive, and isolated loading chamber that is created when in the retention stage loading position. It may be the case that a sample is prepared in the ion beam while the sample is held at low temperature. Such a temperature may be below the dew point of the local atmosphere immediately outside of the apparatus. If the shield retention stage is at a temperature below the local dew point, then exposing it to the atmosphere during loading and unloading may result in water condensation in the loading chamber. Such water condensation would spoil the vacuum conditions maintained in the vacuum chamber if the wet retention stage were moved into the vacuum chamber. In addition, condensation, if allowed to form on the sample, may ruin the sample. After the sample has been processed in the ion beam, it may be moved by the retention stage lifting means and lift drive into the retention stage loading position. In this position the shield retention stage is in thermally conductive contact with a portion of the vacuum chamber. Since the thermal transfer member is no longer in contact with the shield retention stage, the temperature of the shield retention stage is free to rise to the temperature of that portion of the vacuum chamber. Since the temperature of the vacuum chamber is at about the same temperature as the local atmosphere, the shield retention stage, shield, and sample will approach the temperature of the local atmosphere. The thermally conductive contact between the vacuum chamber and the shield retention stage when in the retention stage loading position provides an efficient way to warm up a sample that has been previously cooled while in the retention stage processing position. When the sample, shield, and shield retention stage have warmed up sufficiently, the loading chamber may be re-pressurized to ambient conditions, the chamber cover may be removed, and the shield and sample combination may be removed from the apparatus for microscopic observation elsewhere.

Although the present invention has been described in considerable detail with reference to certain preferred versions thereof, other versions are possible. For example, it may be desirable to combine features shown in various embodiments into a single embodiment. Also, it may be that certain preferred versions have alternatives that may be suitably substituted and achieve similar performance in various embodiments. For example, the chamber cover used to access the loading chamber of the apparatus may satisfy the needed functionality equally well whether it be tethered to the apparatus, attached to the apparatus via hinge, or capable of being entirely removed from the apparatus. These and other equivalents will be readily recognized by those skilled in the art. Therefore, the spirit and scope of the appended claims should not be limited to the description of the preferred versions contained herein.

Any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" in the claims herein is not intended to invoke the provisions of 35 U.S.C. Section 112, Paragraph 6.

The invention claimed is:

1. An ion beam sample preparation apparatus comprising:
   a) an ion beam irradiating means disposed in a vacuum chamber and directing an ion beam toward a shield retention stage;
   b) the shield retention stage being disposed in the vacuum chamber; said shield retention stage comprising a shield retention means having at least a shield releasing position and a shield retaining position;

c) a retention stage lifting means coupled to said shield retention stage and configured to move said shield retention stage between a retention stage loading position and a retention stage processing position, characterized in that when the retention stage lifting means is in said retention stage loading position a substantially vacuum-tight loading chamber is created between the shield retention stage and a portion of the vacuum chamber, and further characterized in that when the retention stage lifting means is in said retention stage loading position a substantially vacuum-tight seal is created between the loading chamber and the portion of the vacuum chamber in which the ion beam irradiating means is disposed;

d) a lift drive coupled to said retention stage lifting means and operable to move said retention stage lifting means between said retention stage loading position and said retention stage processing position;

e) a removable and replaceable chamber cover disposed to allow access to said loading chamber when said retention stage lifting means is held in said retention stage loading position, characterized in that said chamber cover provides a substantially vacuum-tight seal when in place on said vacuum chamber;

f) a vacuum pump means operably connected to both a first pumping manifold and a second pumping manifold, wherein the first pumping manifold is configured to evacuate said vacuum chamber, and wherein the second pumping manifold is configured to evacuate said loading chamber when said retention stage lifting means is in said retention stage loading position.

2. The apparatus of claim 1 further comprising a shield having at least a rigid planar portion, removably and replaceably held in said shield retention stage, said shield further comprising: a proximal sample surface configured to durably adhere the sample to the shield; a first shielding surface disposed in the path of the ion beam and positioned to shield a portion of the ion beam directed at the sample when said shield is held in the shield retaining position of the shield retention means and the retention stage lifting means is held in the retention stage processing position.

3. The apparatus of claim 2 wherein the first shielding surface meets said proximal sample surface at an angle of less than about 90 degrees and more than about 80 degrees.

4. The apparatus of claim 2 wherein the first shielding surface meets said proximal sample surface at an angle of less than about 87 degrees and more than about 83 degrees.

5. The apparatus of claim 2 wherein the first shielding surface is made of non-magnetic material having low sputtering-yield.

6. The apparatus of claim 2 wherein at least a portion of the first shielding surface is made of tantalum or titanium.

7. The apparatus of claim 2 wherein the proximal sample surface has at least one recessed portion configured for the flowing of adhesive between the shield and the sample.

8. The apparatus of claim 2 wherein the shield further comprises:

a) a second shielding surface having a portion disposed in the path of a portion of the ion beam;

b) a shield edge formed where the first shielding surface meets the proximal sample surface; and c) a visible alignment mark on the second shielding surface, configured such that the location of said visible alignment mark is in a predetermined relationship to the region where the ion beam impinges on said shield edge when said shield is held in the shield retaining position of the shield retention means.

9. The apparatus of claim 2 wherein the shield is made of a cladding material joined to a core material such that a portion of the cladding material forms at least a portion of the first shielding surface.

10. The apparatus of claim 9 wherein the cladding material is made of non-magnetic material having low sputtering-yield.

11. The apparatus of claim 10 wherein at least a portion of the cladding material is tantalum or titanium.

12. An ion beam sample preparation apparatus comprising:

a) an ion beam irradiating means disposed in a vacuum chamber and directing an ion beam toward a shield retention stage;

b) the shield retention stage being disposed in the vacuum chamber; said shield retention stage comprising a shield retention means having at least a shield releasing position and a shield retaining position;

c) a retention stage lifting means coupled to said shield retention stage and configured to move said shield retention stage between a retention stage loading position and a retention stage processing position, characterized in that when the retention stage lifting means is in said retention stage loading position a substantially vacuum-tight loading chamber is created between the shield retention stage and a portion of the vacuum chamber, and further characterized in that when the retention stage lifting means is in said retention stage loading position a substantially vacuum-tight seal is created between the loading chamber and the portion of the vacuum chamber in which the ion beam irradiating means is disposed;

d) a lift drive coupled to said retention stage lifting means and operable to move said retention stage lifting means between said retention stage loading position and said retention stage processing position;

e) a removable and replaceable chamber cover disposed to allow access to said loading chamber when said retention stage lifting means is held in said retention stage loading position, characterized in that said chamber cover provides a substantially vacuum-tight seal when in place on said vacuum chamber;

f) a vacuum pump means operably connected to both a first pumping manifold and a second pumping manifold, wherein the first pumping manifold is configured to evacuate said vacuum chamber, and wherein the second pumping manifold is configured to evacuate said loading chamber when said retention stage lifting means is in said retention stage loading position;

g) a thermal transfer member in thermally conductive contact with the shield retention stage;

h) a heat sink means configured to conduct heat away from said thermal transfer member.

13. The apparatus of claim 12 further comprising a shield having at least a rigid planar portion, removably and replaceably held in said shield retention stage, said shield further comprising: a proximal sample surface configured to durably adhere the sample to the shield; a first shielding surface disposed in the path of the ion beam and positioned to shield a portion of the ion beam directed at the sample when said shield is held in the shield retaining position of the shield retention means and the retention stage lifting means is held in the retention stage processing position.

14. The apparatus of claim 13 wherein the first shielding surface is made of non-magnetic material with low sputtering-yield.

15. The apparatus of claim 13 wherein the heat sink means is configured to use nitrogen to conduct heat away from the thermal transfer member.

16. The apparatus of claim 13 wherein the shield is made of a material having high thermal conductivity.

17. The apparatus of claim 13 wherein the shield is made of a cladding material joined to a core material such that a portion of the cladding material forms at least a portion of the first shielding surface.

18. The apparatus of claim 17 wherein the core material comprises copper.

19. An ion beam sample preparation apparatus comprising:
   a) an ion beam irradiating means disposed in a vacuum chamber and directing an ion beam toward a shield retention stage;
   b) the shield retention stage being disposed in the vacuum chamber; said shield retention stage comprising a shield retention means having at least a shield releasing position and a shield retaining position;
   c) a retention stage lifting means coupled to said shield retention stage and configured to move said shield retention stage between a retention stage loading position and a retention stage processing position, characterized in that when the retention stage lifting means is in said retention stage loading position a substantially vacuum-tight loading chamber is created between the shield retention stage and a portion of the vacuum chamber, further characterized in that when the retention stage lifting means is in said retention stage loading position, a substantially vacuum-tight seal is created between the loading chamber and the portion of the vacuum chamber in which the ion beam irradiating means is disposed, and further characterized in that when the retention stage lifting means is in said retention stage loading position said shield retention stage is in thermally conductive contact with a portion of said vacuum chamber;
   d) a lift drive coupled to said retention stage lifting means and operable to move said retention stage lifting means between said retention stage loading position and said retention stage processing position;
   e) a removable and replaceable chamber cover disposed to allow access to said loading chamber when said retention stage lifting means is held in said retention stage loading position, characterized in that said chamber cover provides a substantially vacuum-tight seal when in place on said vacuum chamber;
   f) a vacuum pump means operably connected to both a first pumping manifold and a second pumping manifold, wherein the first pumping manifold is configured to evacuate said vacuum chamber, and wherein the second pumping manifold is configured to evacuate said loading chamber when said retention stage lifting means is in said retention stage loading position;
   g) a thermal transfer member disposed so that said thermal transfer member is in thermally conductive contact with the shield retention stage when said retention stage lifting means is held in said retention stage processing position, and further disposed so that said thermal transfer member is not in thermally conductive contact with the shield retention stage when said retention stage lifting means is held in said retention stage loading position;
   h) a heat sink means configured to conduct heat away from said thermal transfer member.

20. The apparatus of claim 19 further comprising a shield having at least a rigid planar portion, removably and replaceably held in said shield retention stage, said shield further comprising: a proximal sample surface configured to durably adhere the sample to the shield; a first shielding surface disposed in the path of the ion beam and positioned to shield a portion of the ion beam directed at the sample when said shield is held in the shield retaining position of the shield retention means and the retention stage lifting means is held in the retention stage processing position.

21. The apparatus of claim 20 wherein the first shielding surface is made of non-magnetic material with low sputtering-yield.

22. The apparatus of claim 20 wherein the heat sink means is configured to use nitrogen to conduct heat away from the thermal transfer member.

23. The apparatus of claim 20 wherein the shield is made of a material having high thermal conductivity.

24. The apparatus of claim 20 wherein the shield is made of a cladding material joined to a core material such that a portion of the cladding material forms at least a portion of the first shielding surface.

25. The apparatus of claim 24 wherein the core material comprises copper.

* * * * *